US012745893B2

(12) United States Patent
Saito

(10) Patent No.: US 12,745,893 B2
(45) Date of Patent: Sep. 29, 2026

(54) PROCESSOR DEVICE, METHOD OF OPERATING THE SAME, AND ENDOSCOPE SYSTEM

(71) Applicant: FUJIFILM Corporation, Tokyo (JP)

(72) Inventor: Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 353 days.

(21) Appl. No.: 18/519,075

(22) Filed: Nov. 27, 2023

(65) Prior Publication Data

US 2024/0081616 A1 Mar. 14, 2024

Related U.S. Application Data

(63) Continuation of application No. PCT/JP2022/020364, filed on May 16, 2022.

(30) Foreign Application Priority Data

Jun. 1, 2021 (JP) ................................ 2021-092261

(51) Int. Cl.
*A61B 1/00* (2006.01)
*A61B 1/04* (2006.01)
(Continued)

(52) U.S. Cl.
CPC .......... *A61B 1/000095* (2022.02); *A61B 1/04* (2013.01); *A61B 1/0638* (2013.01);
(Continued)

(58) Field of Classification Search
CPC ... A61B 1/000095; A61B 1/04; A61B 1/0638; A61B 1/0655; A61B 1/0684;
(Continued)

(56) References Cited

U.S. PATENT DOCUMENTS 9,675,287 B2 * 6/2017 Saito .................. A61B 5/14551
9,681,831 B2 * 6/2017 Saito .................... A61B 1/0638
(Continued)

FOREIGN PATENT DOCUMENTS

EP 2449950 A1 * 5/2012 ........... A61B 1/0646
EP 2912991 A1 * 9/2015 ....... A61B 1/000094
(Continued)

OTHER PUBLICATIONS

"International Search Report (Form PCT/ISA/210) of PCT/JP2022/020364", mailed on Jun. 28, 2022, with English translation thereof, pp. 1-5.

(Continued)

*Primary Examiner* — Navin Natnithithadha

(74) *Attorney, Agent, or Firm* — JCIPRNET

(57) ABSTRACT

Oxygen saturation is calculated on the basis of a calculation value with reference to an oxygen saturation calculation table TBL. A specific colorant concentration of a specific colorant other than hemoglobin is calculated on the basis of B3 image signals and G1 image signals. Whether or not a first difference D1 between the specific colorant concentration and a reference concentration is in a specific range is monitored. A correction notification related to correction of the oxygen saturation calculation table TBL is performed on the basis of a result of the monitoring of the specific colorant concentration.

8 Claims, 12 Drawing Sheets

(51) Int. Cl.

| | |
|---|---|
| ***A61B 1/06*** | (2006.01) |
| ***A61B 5/026*** | (2006.01) |
| ***A61B 5/1455*** | (2006.01) |
| ***A61B 5/1459*** | (2006.01) |
| ***A61B 90/00*** | (2016.01) |

(52) U.S. Cl.

CPC .......... *A61B 1/0655* (2022.02); *A61B 1/0684* (2013.01); *A61B 5/0261* (2013.01); *A61B 5/14552* (2013.01); *A61B 5/1459* (2013.01); *A61B 2090/3937* (2016.02)

(58) Field of Classification Search

CPC . A61B 5/0261; A61B 5/14552; A61B 5/1459; A61B 2090/3937; A61B 1/00186; A61B 1/000094; A61B 1/044; A61B 5/14551

See application file for complete search history.

(56) References Cited

U.S. PATENT DOCUMENTS

| | | | | | |
|---|---|---|---|---|---|
| 9,801,573 | B2 * | 10/2017 | Saito | A61B 5/1459 | |
| 9,918,613 | B2 * | 3/2018 | Saito | A61B 1/0653 | |
| 10,939,856 | B2 * | 3/2021 | Saito | G02B 23/24 | |
| 2012/0116192 | A1 * | 5/2012 | Saito | A61B 1/0646 | 600/323 |
| 2012/0157768 | A1 * | 6/2012 | Saito | A61B 1/0653 | 600/109 |
| 2013/0211217 | A1 * | 8/2013 | Yamaguchi | A61B 5/7278 | 600/327 |
| 2014/0152790 | A1 * | 6/2014 | Saito | A61B 5/1459 | 348/68 |
| 2014/0155717 | A1 * | 6/2014 | Saito | G06T 7/0012 | 600/339 |
| 2015/0238126 | A1 * | 8/2015 | Saito | A61B 5/1459 | 600/339 |
| 2015/0238127 | A1 * | 8/2015 | Saito | H04N 23/10 | 600/431 |
| 2017/0014055 | A1 | 1/2017 | Otani | | |
| 2018/0020903 | A1 | 1/2018 | Saito | | |
| 2020/0352488 | A1 * | 11/2020 | Saito | A61B 1/018 | |

FOREIGN PATENT DOCUMENTS

| | | | | | |
|---|---|---|---|---|---|
| EP | 2912992 | A1 * | 9/2015 | H04N 23/555 |
| EP | 2912991 | B1 * | 9/2016 | A61B 1/000094 |
| EP | 2912992 | B1 * | 9/2016 | H04N 25/531 |
| EP | 2912990 | B1 * | 12/2018 | A61B 5/0075 |
| JP | 2015160013 | | 9/2015 | |
| JP | 2015160013 | A * | 9/2015 | H04N 23/555 |
| JP | 2015177961 | A * | 10/2015 | A61B 1/000094 |
| JP | 2016007353 | A * | 1/2016 | A61B 1/04 |
| JP | 6010571 | B2 * | 10/2016 | H04N 23/74 |
| JP | 6039639 | | 12/2016 | |
| JP | 6039639 | B2 * | 12/2016 | A61B 1/000094 |
| JP | 2017018503 | | 1/2017 | |
| JP | 2018108314 | | 7/2018 | |
| JP | 6412252 | | 10/2018 | |
| JP | WO2018043728 | A1 * | 3/2019 | A61B 1/000094 |
| WO | WO-2018043728 | A1 * | 3/2018 | A61B 1/000094 |

OTHER PUBLICATIONS

"Written Opinion of the International Searching Authority (Form PCT/ISA/237) of PCT/JP2022/020364", mailed on Jun. 28, 2022, with English translation thereof, pp. 1-8.

* cited by examiner

FIG. 4

| ILLUMINATION | IMAGING (IMAGE SIGNAL) |
|---|---|
| EMISSION OF FIRST BLUE LIGHT<br>EMISSION OF GREEN LIGHT<br>EMISSION OF RED LIGHT | (Bc,Gc,Rc) |

FIG. 5

| | ILLUMINATION | IMAGE SIGNAL |
|---|---|---|
| FIRST FRAME | EMISSION OF FIRST BLUE LIGHT<br>EMISSION OF GREEN LIGHT<br>EMISSION OF RED LIGHT | (B1,G1,R1) |
| SECOND FRAME | EMISSION OF SECOND BLUE LIGHT<br>EMISSION OF GREEN LIGHT<br>EMISSION OF RED LIGHT | (B2,G2,R2) |
| THIRD FRAME | EMISSION OF GREEN LIGHT | (B3,G3,R3) |

PROCESSOR DEVICE, METHOD OF OPERATING THE SAME, AND ENDOSCOPE SYSTEM

CROSS-REFERENCE TO RELATED APPLICATIONS

This application is a Continuation of PCT International Application No. PCT/JP2022/020364 filed on 16 May 2022, which claims priority under 35 U.S.C § 119(a) to Japanese Patent Application No. 2021-092261 filed on 1 Jun. 2021. The above application is hereby expressly incorporated by reference, in its entirety, into the present application.

BACKGROUND OF THE INVENTION

1. Field of the Invention

The present invention relates to a processor device that calculates oxygen saturation of a subject of observation, a method of operating the processor device, and an endoscope system.

2. Description of the Related Art

In recent years, oxygen saturation imaging has been known in medical fields in which endoscopes are used. In the oxygen saturation imaging, hemoglobin oxygen saturation is calculated from a small amount of spectral information about visible light. In a case where a specific colorant, such as a yellow colorant, is present in a tissue to be observed in addition to hemoglobin, spectral signals are affected by light absorption of the specific colorant in the calculation of oxygen saturation. For this reason, there is a problem in that calculated oxygen saturation deviates. In order to solve this problem, imaging for correction for acquiring spectral characteristics of the tissue to be observed is performed before observation of oxygen saturation, and an algorithm for calculating oxygen saturation is corrected on the basis of signals obtained from the imaging for correction and is then used for the calculation of oxygen saturation (see JP6412252B2 (corresponding to US2018/0020903A1) and JP6039639B2 (corresponding to US2015/0238126A1)).

SUMMARY OF THE INVENTION

In the correction method performed before the calculation of oxygen saturation as described above, it is premised that the same portion on the tissue is imaged at a time of the imaging for correction and at a time of subsequent observation. However, in a case where the correction method is actually used in clinical use, it is assumed that once the imaging for correction is performed, other portions are also observed, and if in such cases a portion in which spectral characteristics of a tissue different from those in an initial correction are observed, there is a possibility that a calculated oxygen saturation value deviates from a true value.

An object of the present invention is to provide a processor device that allows oxygen saturation to be calculated with high accuracy even in a case where a plurality of tissues having different spectral characteristics are to be observed, a method of operating the processor device, and an endoscope system.

A processor device according to an aspect of the present invention comprises a processor. The processor acquires a first image signal that corresponds to a first wavelength range having a sensitivity to a specific colorant concentration of a specific colorant other than blood hemoglobin among colorants included in a subject of observation, a second image signal that corresponds to a second wavelength range having a sensitivity to oxygen saturation of blood hemoglobin, a third image signal that corresponds to a third wavelength range having a sensitivity to a blood volume, and a fourth image signal that corresponds to a fourth wavelength range having a wavelength longer than wavelengths of the first wavelength range, the second wavelength range, and the third wavelength range; calculates a calculation value via calculation processing based on the second image signal, the third image signal, and the fourth image signal; calculates the oxygen saturation on the basis of the calculation value with reference to an oxygen saturation calculation table; calculates the specific colorant concentration on the basis of the first image signal and the third image signal; monitors the specific colorant concentration during the calculation of the oxygen saturation; and performs a correction notification related to correction of the oxygen saturation calculation table on the basis of a result of the monitoring of the specific colorant concentration.

It is preferable that the processor calculates a first difference or a first ratio between each of specific colorant concentrations sequentially calculated and a reference concentration predetermined for the specific colorant concentration and performs the correction notification in a case where the first difference or the first ratio is out of a specific range. It is preferable that the processor calculates a specific colorant concentration-average value that is an average value of specific colorant concentrations calculated in a certain time, calculates a second difference or a second ratio between the specific colorant concentration-average value and a reference concentration predetermined for the specific colorant concentration, and performs the correction notification in a case where the second difference or the second ratio is out of a specific range.

It is preferable that the reference concentration is the specific colorant concentration obtained at a timing when the oxygen saturation calculation table is corrected. It is preferable that the reference concentration is predetermined for each patient or each site. It is preferable that the specific colorant is a yellow colorant. It is preferable that the first wavelength range is 450±10 nm, the second wavelength range is 470±10 nm, the third wavelength range is a green light wavelength range, and the fourth wavelength range is a red light wavelength range.

An endoscope system according to another aspect of the present invention comprises: the processor device according to the aspect of the present invention; a light source device that includes a light source unit and a light source processor, the light source unit including a first semiconductor light source emitting first blue light, a second semiconductor light source emitting second blue light having a wavelength longer than a wavelength of the first blue light, a third semiconductor light source emitting green light, and a fourth semiconductor light source emitting red light, and the light source processor controlling turn-on and turn-off of the first semiconductor light source, the second semiconductor light source, the third semiconductor light source, and the fourth semiconductor light source; and an endoscope that includes an imaging sensor provided with a B color filter having a blue light transmission range, a G color filter having a green light transmission range, and an R color filter having a red light transmission range. The first wavelength range is a wavelength range of light, which has been transmitted through the B color filter, of the green light; the second wavelength range is a wavelength range of light, which has been transmitted through the B color filter, of the second blue light; the third wavelength range is a wavelength range of light, which has been transmitted through the G color filter, of the green light; and the fourth wavelength range is a wavelength range of light, which has been transmitted through the R color filter, of the red light.

It is preferable that the blue light transmission range is 380 to 560 nm, the green light transmission range is 450 to 630 nm, and the red light transmission range is 580 to 760 nm.

A method of operating a processor device according to still another aspect of the present invention comprises, via a processor: a step of acquiring a first image signal that corresponds to a first wavelength range having a sensitivity to a specific colorant concentration of a specific colorant other than blood hemoglobin among colorants included in a subject of observation, a second image signal that corresponds to a second wavelength range having a sensitivity to oxygen saturation of blood hemoglobin, a third image signal that corresponds to a third wavelength range having a sensitivity to a blood volume, and a fourth image signal that corresponds to a fourth wavelength range having a wavelength longer than wavelengths of the first wavelength range, the second wavelength range, and the third wavelength range; a step of calculating a calculation value via calculation processing based on the second image signal, the third image signal, and the fourth image signal; a step of calculating the oxygen saturation on the basis of the calculation value with reference to an oxygen saturation calculation table; a step of calculating the specific colorant concentration on the basis of the first image signal and the third image signal; a step of monitoring the specific colorant concentration during the calculation of the oxygen saturation; and a step of performing a correction notification related to correction of the oxygen saturation calculation table on the basis of a result of the monitoring of the specific colorant concentration.

According to the present invention, it is possible for oxygen saturation to be calculated with high accuracy even in a case where a plurality of tissues having different spectral characteristics are to be observed.

BRIEF DESCRIPTION OF THE DRAWINGS

FIG. 4 is a diagram illustrating emission of illumination light and imaging of a subject of observation in a normal mode.

FIG. 5 is a diagram illustrating emission of illumination light and imaging of a subject of observation in an oxygen saturation mode.

DESCRIPTION OF THE PREFERRED EMBODIMENTS

First Embodiment

Figure 1:
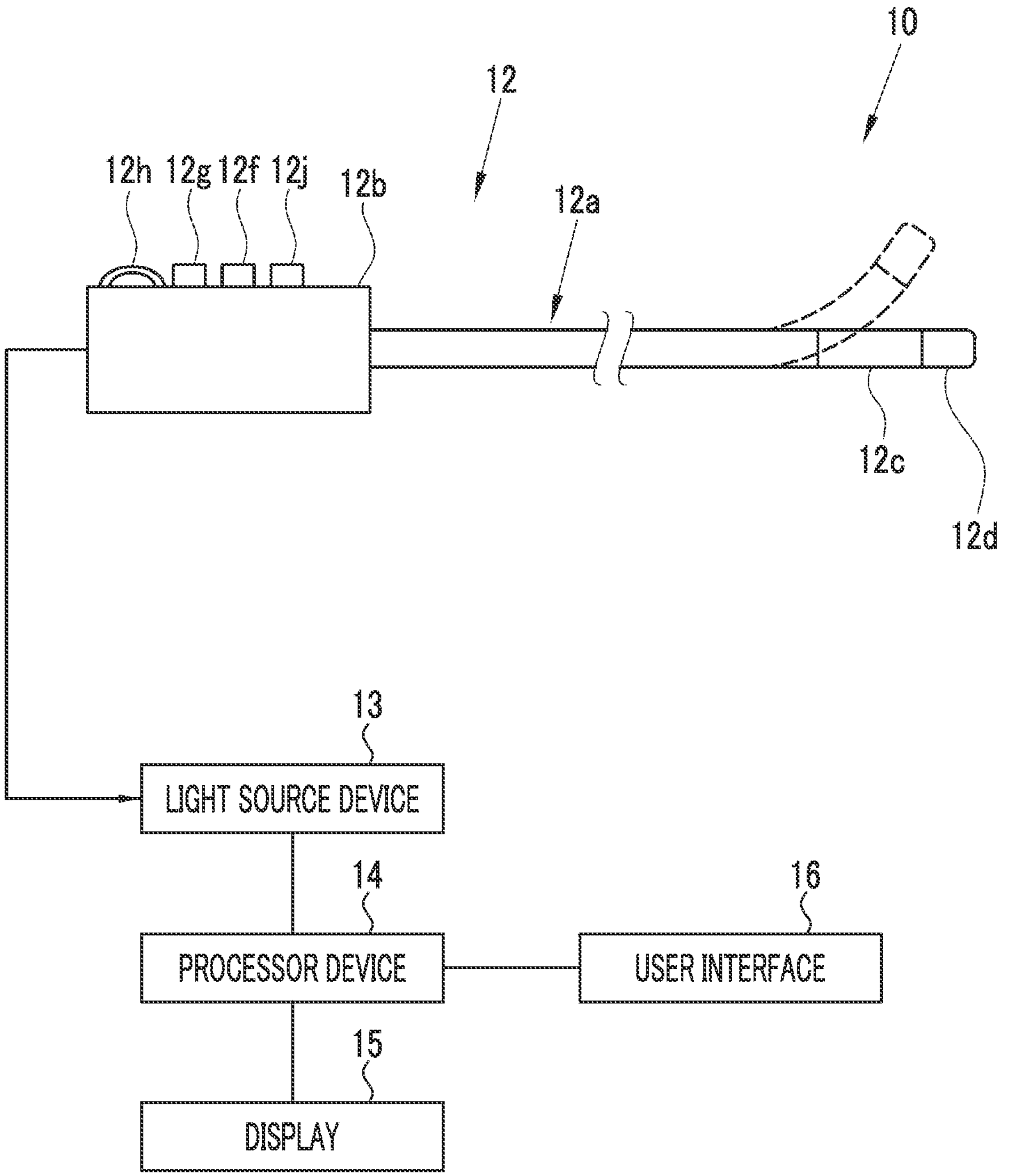
FIG. 1 is an external view of an endoscope system.

As shown in FIG. 1, an endoscope system 10 includes an endoscope 12, a light source device 13, a processor device 14, a display 15, and a user interface 16. The endoscope 12 is optically connected to the light source device 13, and is electrically connected to the processor device 14. The light source device 13 supplies illumination light to the endoscope 12.

The endoscope 12 is used to illuminate a subject of observation with illumination light and to image the subject of observation to acquire an endoscopic image. The endoscope 12 includes an insertion part 12*a* that is to be inserted into a body of the subject of observation, an operation part 12*b* that is provided at a proximal end portion of the insertion part 12*a*, and a bendable part 12*c* and a distal end part 12*d* that are provided on a distal end side of the insertion part 12*a*. In a case where the operation part 12*b* is operated, the bendable part 12*c* is operated to be bent. The distal end part 12*d* irradiates the subject of observation with illumination light and receives light reflected from the subject of observation to image the subject of observation. As the bendable part 12*c* is operated to be bent, the distal end part 12*d* is made to face in a desired direction. The operation part 12*b* is provided with a mode selector switch 12*f* that is used for an operation for switching a mode, a still image-acquisition instruction switch 12*g* that is used to give an instruction to acquire a still image of the subject of observation, and a zoom operation part 12*h* that is used for an operation of a zoom lens 21*b*.

The processor device 14 is electrically connected to the display 15 and the user interface 16. The processor device 14 receives image signals output from the endoscope 12, and performs various types of processing on the basis of the image signals. The display 15 outputs and displays an image, information, or the like of the subject of observation that is processed by the processor device 14. The user interface 16 includes a keyboard, a mouse, a touch pad, a microphone, and the like and has a function to receive an input operation, such as function settings.

The endoscope system 10 includes two modes, that is, a normal mode and an oxygen saturation mode, and these two modes are switched in a case where a user operates the mode selector switch 12*f*. In the normal mode, a normal image having a natural tone, which is obtained by imaging of a subject of observation using white light as illumination light, is displayed on the display 15. In the oxygen saturation mode, oxygen saturation of the subject of observation is calculated on the basis of image signals output from the endoscope 12 with reference to an oxygen saturation calculation table TBL. Then, an oxygen saturation image in which the calculated oxygen saturation is made as an image with a pseudo color or the like is displayed on the display 15.

In a case where a tissue color correction button 12*j* is operated during execution of the oxygen saturation mode, a tissue color correction mode is executed. In the tissue color correction mode, the oxygen saturation calculation table TBL is corrected to calculate oxygen saturation corresponding to a tissue color that is being observed. Then, oxygen saturation is calculated in the oxygen saturation mode using the corrected oxygen saturation calculation table TBL. Further, a specific colorant concentration is monitored during the calculation of oxygen saturation, and a correction notification related to the correction of the oxygen saturation calculation table TBL is made according to the result of the monitoring.

Figure 2:
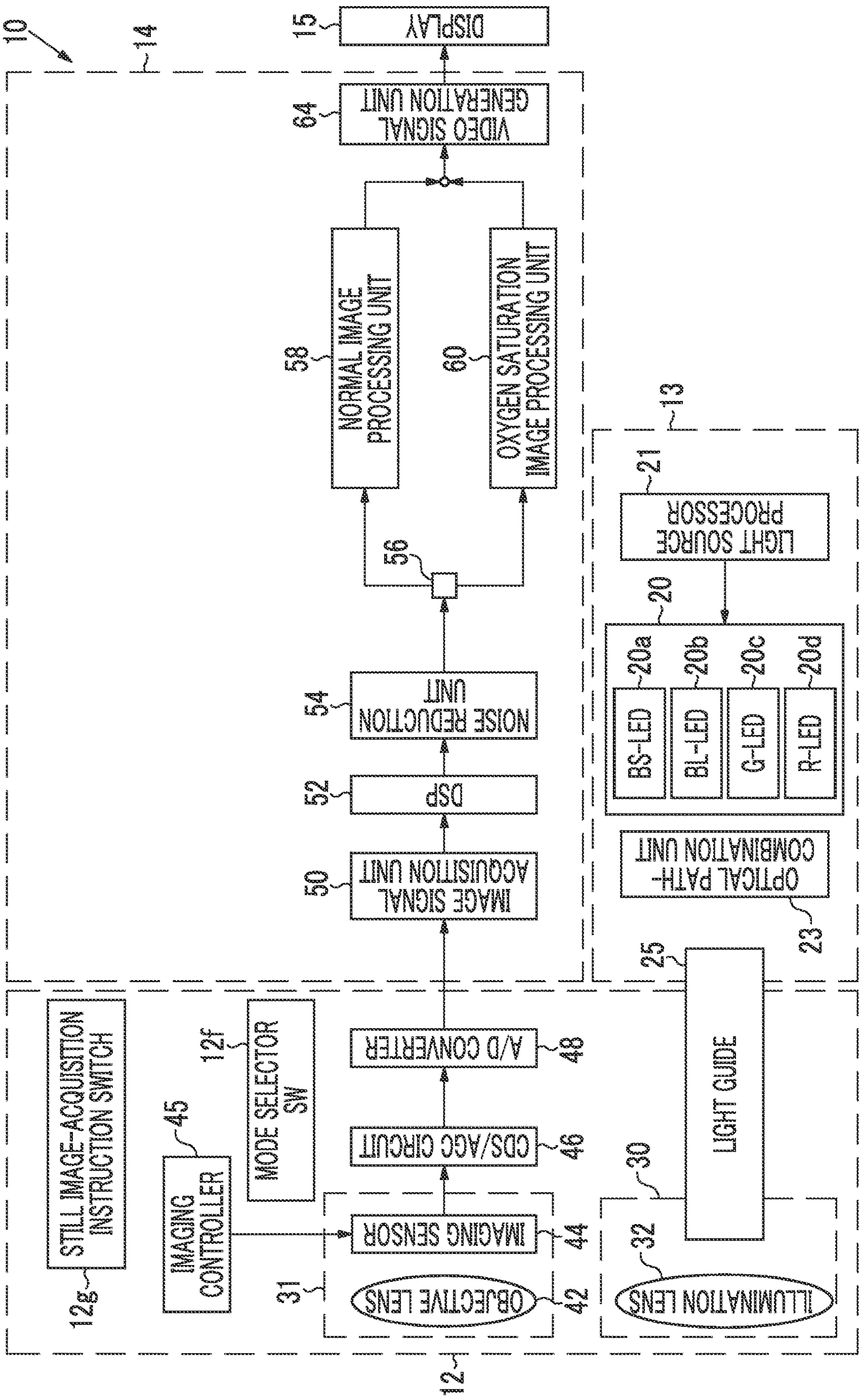
FIG. 2 is a block diagram showing functions of the endoscope system according to a first embodiment.

As shown in FIG. 2, the light source device 13 comprises a light source unit 20 and a light source processor 21 that controls the light source unit 20. The light source unit 20 includes, for example, a plurality of semiconductor light sources, turns on or off each of these semiconductor light sources, and emits illumination light, which illuminates the subject of observation, by controlling the amount of light emitted from each semiconductor light source, in a case where each semiconductor light source is turned on. In the present embodiment, the light source unit 20 includes four color LEDs, that is, a blue short-wavelength light emitting diode (BS-LED) 20*a*, a blue long-wavelength light emitting diode (BL-LED) 20*b*, a green light emitting diode (G-LED) 20*c*, and a red light emitting diode (R-LED) 20*d*.

The BS-LED 20*a* (first semiconductor light source) emits first blue light BS having a wavelength of 450 nm±10 nm. The BL-LED 20*b* (second semiconductor light source) emits second blue light BL having a wavelength of 470 nm±10 nm. The G-LED 20*c* (third semiconductor light source) emits green light G having a wavelength in a green light wavelength range. It is preferable that a central wavelength of the green light G is 540 nm. The R-LED 20*d* (fourth semiconductor light source) emits red light R having a wavelength in a red light wavelength range. It is preferable that a central wavelength of the red light R is 620 nm. A central wavelength and a peak wavelength of each of the LEDs 20*a* to 20*d* may be equal to each other or different from each other.

The light source processor 21 independently inputs control signals to the respective LEDs 20*a* to 20*d* to independently control the turn-on or turn-off of the respective LEDs 20*a* to 20*d*, the amounts of the lights that are emitted from the respective LEDs 20*a* to 20*d* in a case where the respective LEDs 20*a* to 20*d* are turned on, and the like. The control of the turn-on or turn-off in the light source processor 21 differs depending on each mode. In the normal mode, the BS-LED 20*a*, the G-LED 20*c*, and the R-LED 20*d* are simultaneously turned on to simultaneously emit the first blue light BS, the green light G, and the red light R (see the drawing).

In the oxygen saturation mode or the tissue color correction mode, lights having different light emission patterns and corresponding to three frames are repeatedly emitted (see the drawing). In the first frame, the BS-LED 20*a*, the G-LED 20*c*, and the R-LED 20*d* are simultaneously turned on to simultaneously emit the first blue light BS, the green light G, and the red light R. In the second frame, the BL-LED 20*b*, the G-LED 20*c*, and the R-LED 20*d* are simultaneously turned on to simultaneously emit the second blue light BL, the green light G, and the red light R. In the third frame, the G-LED 20*c* is turned on to emit the green light G.

Light emitted from each of the LEDs 20*a* to 20*d* is incident on a light guide 25 via an optical path-combination unit 23 that is formed of a mirror, a lens, and the like. The light guide 25 is built in the endoscope 12 and a universal cord (a cord connecting the endoscope 12 to the light source device 13 and the processor device 14). The light guide 25 propagates light, which is emitted from the optical path-combination unit 23, up to the distal end part 12*d* of the endoscope 12.

The distal end part 12*d* of the endoscope 12 is provided with an illumination optical system 30 and an imaging optical system 31. The illumination optical system 30 includes an illumination lens 32, and the subject of observation is irradiated with the illumination light propagated by the light guide 25 via the illumination lens 32. The imaging optical system 31 includes an objective lens 42 and an imaging sensor 44. Light reflected from the subject of observation, which is irradiated with the illumination light, is incident on the imaging sensor 44 via the objective lens 42. Accordingly, an image of the subject of observation is formed on the imaging sensor 44.

The imaging sensor 44 is a color imaging sensor that images the subject of observation which is being illuminated with the illumination light. Each pixel of the imaging sensor 44 includes any one of a blue pixel (B pixel) including a blue (B) color filter, a green pixel (G pixel) including a green (G) color filter, or a red pixel (R pixel) including a red (R) color filter. For example, it is preferable that the imaging sensor 44 is a color imaging sensor having a Bayer arrangement in which a ratio of the numbers of B pixels, G pixels, and R pixels is 1:2:1.

Figure 3:
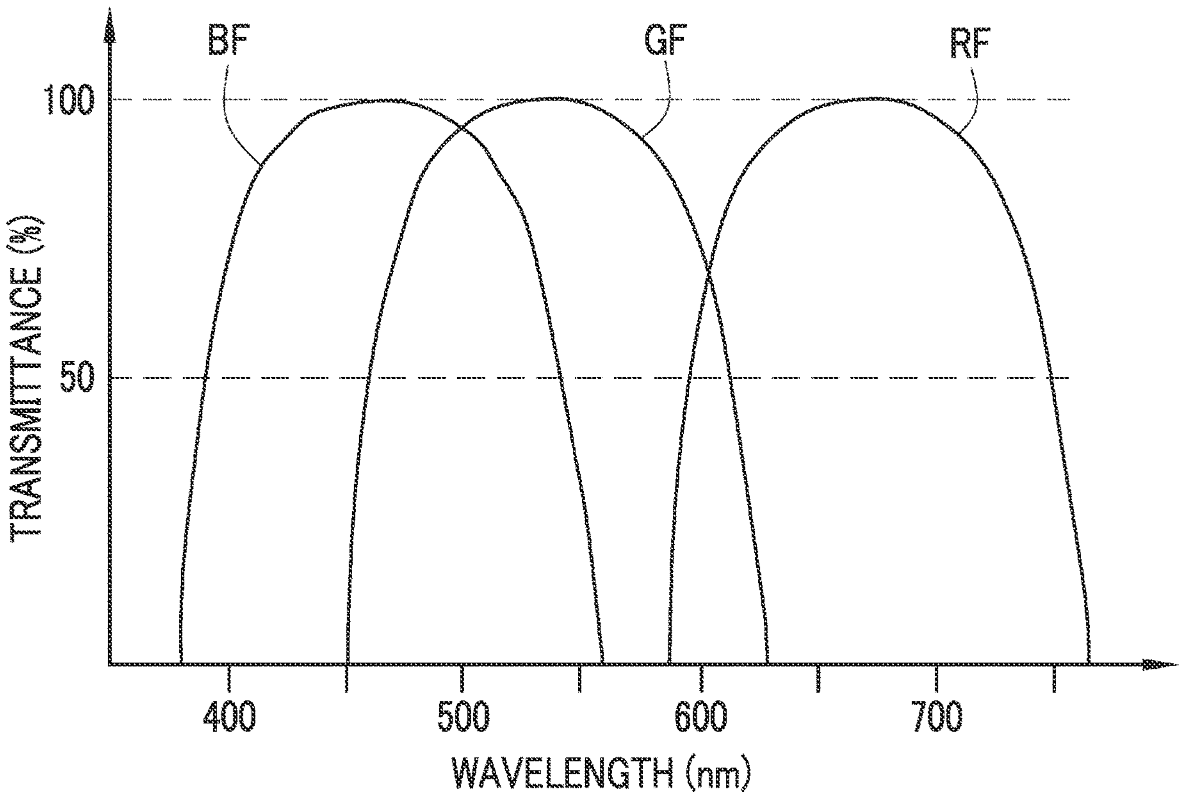
FIG. 3 is a graph showing spectral sensitivity of an imaging sensor.

As shown in FIG. 3, the B color filter BF mainly transmits light having a blue light wavelength range, specifically, light having a wavelength range of 380 to 560 nm (blue light transmission range). A peak wavelength at which transmittance is at its maximum is present near a wavelength range of 460 to 470 nm. The G color filter GF mainly transmits light having a green light wavelength range, specifically, light having a wavelength range of 450 to 630 nm (green light transmission range). The R color filter RF mainly transmits light having a red light wavelength range, specifically, light having a wavelength range of 580 to 760 nm (red light transmission range).

A charge coupled device (CCD) imaging sensor or a complementary metal-oxide-semiconductor (CMOS) imaging sensor can be used as the imaging sensor 44. Further, a complementary color imaging sensor, which comprises complementary color filters corresponding to C (cyan), M (magenta), Y (yellow), and G (green), may be used instead of the primary color imaging sensor 44. In a case where a complementary color imaging sensor is used, image signals corresponding to four colors of C, M, Y, and G are output. Accordingly, the image signals corresponding to four colors of C, M, Y, and G are converted into image signals corresponding to three colors of R, G, and B by complementary color-primary color conversion, so that image signals corresponding to the same respective colors of R, G, and B as those of the imaging sensor 44 can be obtained.

The imaging sensor 44 is driven and controlled by an imaging controller 45. The control of each mode in the imaging controller 45 will be described later. A correlated double sampling/automatic gain control (CDS/AGC) circuit 46 performs correlated double sampling (CDS) or automatic gain control (AGC) on analog image signals that are obtained from the imaging sensor 44. The image signals, which have been transmitted via the CDS/AGC circuit 46, are converted into digital image signals by an analog/digital (A/D) converter 48. The digital image signals, which have been subjected to A/D conversion, are input to the processor device 14.

The processor device 14 comprises an image signal acquisition unit 50, a digital signal processor (DSP) 52, a noise reduction unit 54, an image processing switching unit 56, a normal image processing unit 58, an oxygen saturation image processing unit 60, and a video signal generation unit 64. In the processor device 14, programs related to various types of processing are incorporated into a program memory (not shown). The programs incorporated into the program memory are executed by a central controller (not shown) formed of a processor, so that the functions of the image signal acquisition unit 50, the DSP 52, the noise reduction unit 54, the image processing switching unit 56, the normal image processing unit 58, the oxygen saturation image processing unit 60, and the video signal generation unit 64 are realized. Accordingly, the functions of a calculation value-calculation section 70, an oxygen saturation-calculation section 71, an image generation section 72, a specific colorant concentration-calculation section 73, a concentration monitoring section 74, and a notification section 75, which are included in the oxygen saturation image processing unit 60 and will be described later, are realized.

The image signal acquisition unit 50 receives image signals input from the endoscope 12, and transmits the received image signals to the DSP 52. The DSP 52 performs various types of signal processing, such as defect correction processing, offset processing, gain correction processing, linear matrix processing, gamma conversion processing, demosaicing processing, and YC conversion processing, on the received image signals. Signals of defective pixels of the imaging sensor 44 are corrected in the defect correction processing. Dark current components are removed from the image signals subjected to the defect correction processing in the offset processing, so that an accurate zero level is set. The image signals, which have been subjected to the offset processing and correspond to each color, are multiplied by a specific gain in the gain correction processing, so that the signal level of each image signal is adjusted. The linear matrix processing for improving color reproducibility is performed on the image signals that have been subjected to the gain correction processing and that correspond to each color.

After that, the brightness or chroma saturation of each image signal is adjusted by the gamma conversion processing. The demosaicing processing (also referred to as equalization processing or demosaicing) is performed on the image signals having been subjected to the linear matrix processing, so that signals corresponding to missing colors in the respective pixels are generated by interpolation. All the pixels are made to have signals corresponding to the respective colors of R, G, and B by the demosaicing processing. The DSP 52 performs the YC conversion processing on the respective image signals subjected to the demosaicing processing, and outputs luminance signals Y, color difference signals Cb, and color difference signals Cr to the noise reduction unit 54.

The noise reduction unit 54 performs noise reduction processing, which is performed using, for example, a moving average method, a median filtering method, or the like, on the image signals that have been subjected to the demosaicing processing and the like by the DSP 52. The image signals from which noise has been removed are input to the image processing switching unit 56.

The image processing switching unit 56 switches a destination, to which the image signals output from the noise reduction unit 54 are to be transmitted, to any one of the normal image processing unit 58 or the oxygen saturation image processing unit 60, depending on a set mode. Specifically, in a case where the endoscope system 10 is set to the normal mode, the image signals output from the noise reduction unit 54 are input to the normal image processing unit 58. Further, in a case where the endoscope system 10 is set to the oxygen saturation mode, the image signals output from the noise reduction unit 54 are input to the oxygen saturation image processing unit 60.

The normal image processing unit 58 further performs color conversion processing, such as 3×3-matrix processing, gradation transformation processing, and three-dimensional look up table (LUT) processing, on Rc image signals, Gc image signals, and Bc image signals that are input and that correspond to one frame. Then, the normal image processing unit 58 performs various types of color enhancement processing on RGB image data subjected to the color conversion processing. The normal image processing unit 58 performs structure enhancement processing, such as spatial frequency enhancement, on the RGB image data subjected to the color enhancement processing. The RGB image data subjected to the structure enhancement processing are input to the video signal generation unit 64 as a normal image.

The oxygen saturation image processing unit 60 calculates oxygen saturation using image signals that are obtained in the oxygen saturation mode. A method of calculating oxygen saturation will be described later. The oxygen saturation image processing unit 60 generates an oxygen saturation image in which the calculated oxygen saturation is made as an image with a pseudo color or the like. This oxygen saturation image is input to the video signal generation unit 64.

The video signal generation unit 64 converts the normal image input from the normal image processing unit 58 or the oxygen saturation image input from the oxygen saturation image processing unit 60 into video signals that allow the normal image or the oxygen saturation image to be displayed as a full-color image on the display 15. The converted video signals are input to the display 15. Accordingly, the normal image or the oxygen saturation image is displayed on the display 15.

The imaging control of each mode in the imaging controller 45 will be described below. As shown in FIG. 4, in the normal mode, the imaging controller 45 controls the imaging sensor 44 so that the imaging sensor 44 images a subject of observation, which is being illuminated with the first blue light BS, the green light G, and the red light R, for each frame. Accordingly, Bc image signals are output from the B pixels of the imaging sensor 44, Gc image signals are output from the G pixels thereof, and Rc image signals are output from the R pixels thereof.

As shown in FIG. 5, in the oxygen saturation mode, in a case where the subject of observation is illuminated with the first blue light BS, the green light G, and the red light R in the first frame, B1 image signals are output from the B pixels of the imaging sensor 44, G1 image signals are output from the G pixels thereof, and R1 image signals are output from the R pixels thereof by the imaging controller 45. In a case where the subject of observation is illuminated with the second blue light BL, the green light G, and the red light R in the second frame, B2 image signals are output from the B pixels of the imaging sensor 44, G2 image signals are output from the G pixels thereof, and R2 image signals are output from the R pixels thereof by the imaging controller 45. In a case where the subject of observation is illuminated with the green light G in the third frame, B3 image signals are output from the B pixels of the imaging sensor 44, G3 image signals are output from the G pixels thereof, and R3 image signals are output from the R pixels thereof by the imaging controller 45.

In the oxygen saturation mode, the B3 image signals, the B2 image signals, the G1 image signals, and the R1 image signals among the image signals corresponding to the three frames are used for the calculation of oxygen saturation and the calculation of a specific colorant concentration. The B3 image signal (first image signal) includes image information about a wavelength range (first wavelength range) of light, which has been transmitted through the B color filter BF, of the green light emitted in the third frame. The B2 image signal (second image signal) includes image information about a wavelength range of light, which has been transmitted through the B color filter BF, of at least the second blue light BL of the light emitted in the second frame. The G1 image signal (third image signal) includes image information about a wavelength range of light, which has been transmitted through the G color filter GF, of at least the green light G of the light emitted in the first frame. The R1 image signal (fourth image signal) includes image information about a wavelength range of light, which has been transmitted through the R color filter RF, of at least the red light R of the light emitted in the first frame.

Figure 6:
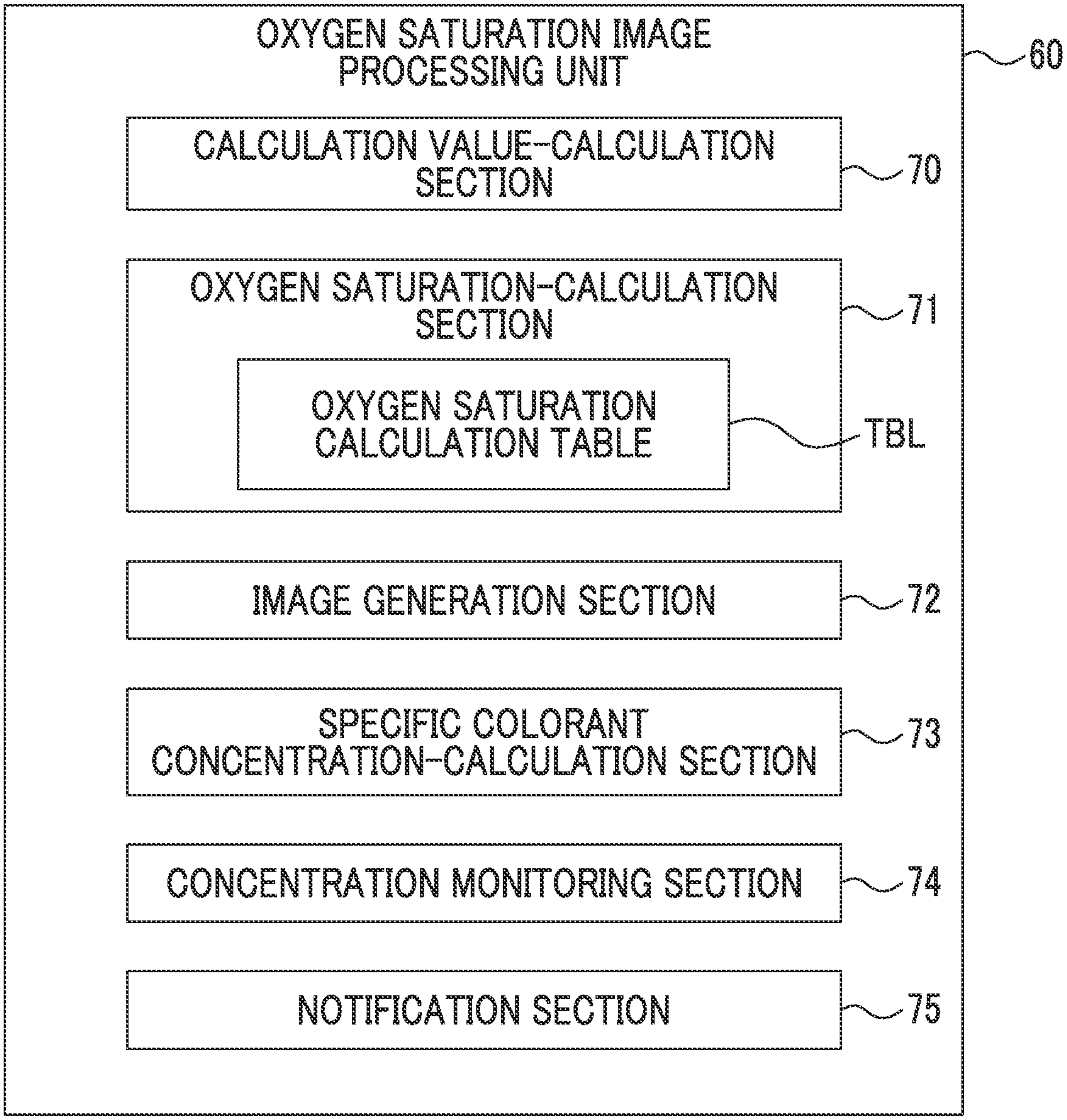
FIG. 6 is a block diagram showing functions of an oxygen saturation image processing unit.

A method of calculating oxygen saturation will be described below. As shown in FIG. 6, the oxygen saturation image processing unit 60 comprises a calculation value-calculation section 70, an oxygen saturation-calculation section 71, an image generation section 72, a specific colorant concentration-calculation section 73, a concentration monitoring section 74, and a notification section 75. The calculation value-calculation section 70 calculates calculation values via calculation processing based on the B2 image signal, the G1 image signal, and the R1 image signal. Specifically, the calculation value-calculation section 70 calculates a signal ratio B2/G1 of the B2 image signal to the G1 image signal and a signal ratio R1/G1 of the R1 image signal to the G1 image signal as calculation values that are used for the calculation of oxygen saturation. It is preferable that the signal ratio B2/G1 and the signal ratio R1/G1 are logarithmized (ln), respectively. Further, color difference signals Cr and Cb, chroma saturation S, a hue H, or the like calculated from the B2 image signal, the G1 image signal, and the R1 image signal may be used as the calculation values.

Figure 7:
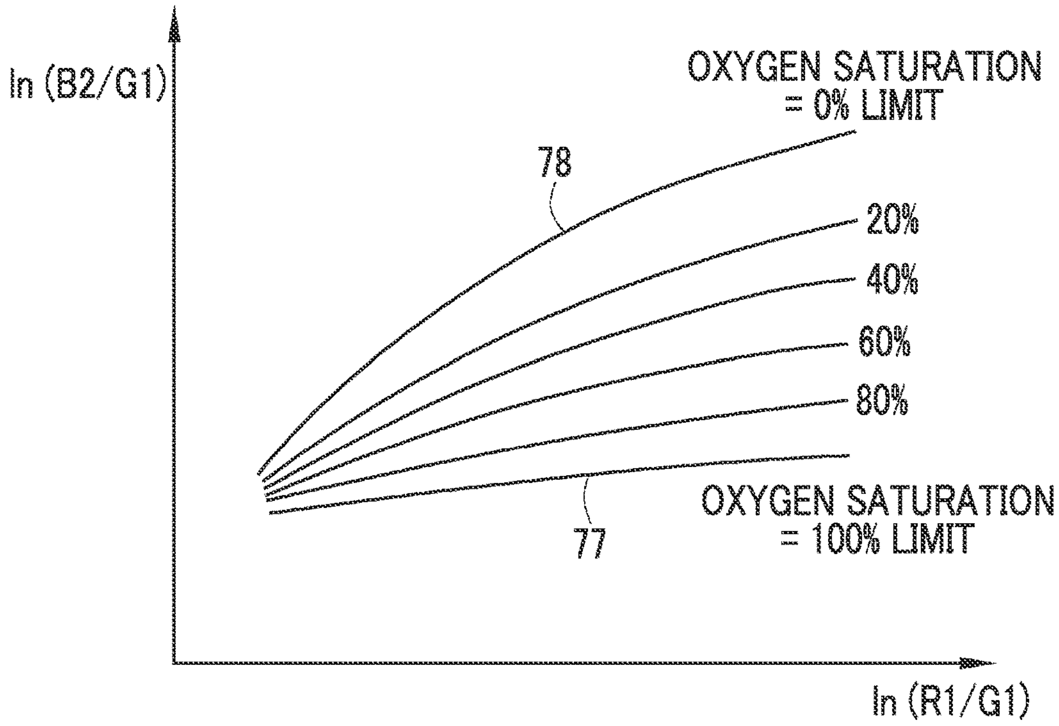
FIG. 7 is a graph showing positions of isolines of oxygen saturation in a two-dimensional space formed by a vertical axis representing ln(B2/G1) and a horizontal axis representing ln(R1/G1).

The oxygen saturation-calculation section 71 calculates oxygen saturation on the basis of the calculation values with reference to the oxygen saturation calculation table TBL. A correlation between the signal ratios B2/G1 and R1/G1 and oxygen saturation is stored in the oxygen saturation calculation table TBL. In a case where the correlation is expressed in a two-dimensional space formed by a vertical axis ln(B2/G1) and a horizontal axis ln(R1/G1), isolines, which connect portions having the same oxygen saturation, are formed substantially in the direction of a horizontal axis as shown in FIG. 7. Further, an isoline is positioned lower in the direction of a vertical axis as oxygen saturation becomes larger. For example, an isoline 77 on which oxygen saturation is 100% is positioned below an isoline 78 on which oxygen saturation is 0%.

Figure 8A:
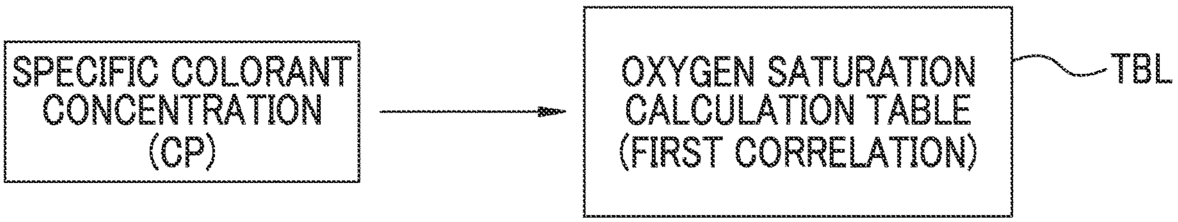
FIGS. 8A and 8B are diagrams illustrating a method of correcting an oxygen saturation calculation table.
Figure 8B:
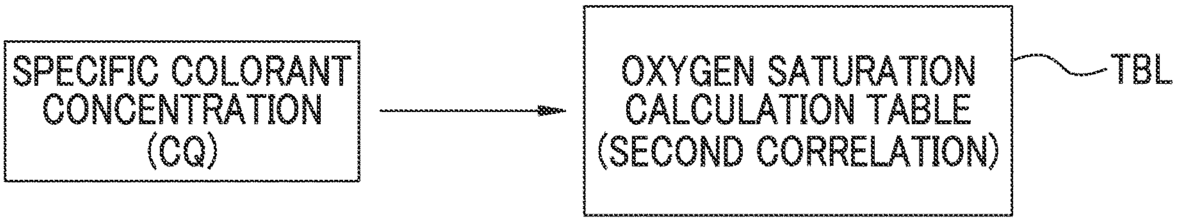

The contents of the oxygen saturation calculation table TBL are adapted to be capable of being corrected according to the specific colorant (a yellow colorant or the like) affecting the calculation of oxygen saturation so that a correlation between the signal ratios B2/G1 and R1/G1 and oxygen saturation can be changed. The correction of the oxygen saturation calculation table TBL is performed according to the operation of the tissue color correction button 12*j*. The change of the correlation corresponds to the adjustment of intervals, positions, and the like of the isolines shown in FIG. 7. For example, in a case where the specific colorant concentration is a concentration CP, the correlation of the oxygen saturation calculation table TBL is changed into a first correlation as shown in FIG. 8A. Further, in a case where the specific colorant concentration is a concentration CQ different from the concentration CP, the correlation of the oxygen saturation calculation table TBL is changed into a second correlation different from the first correlation as shown in FIG. 8B.

Figure 9:
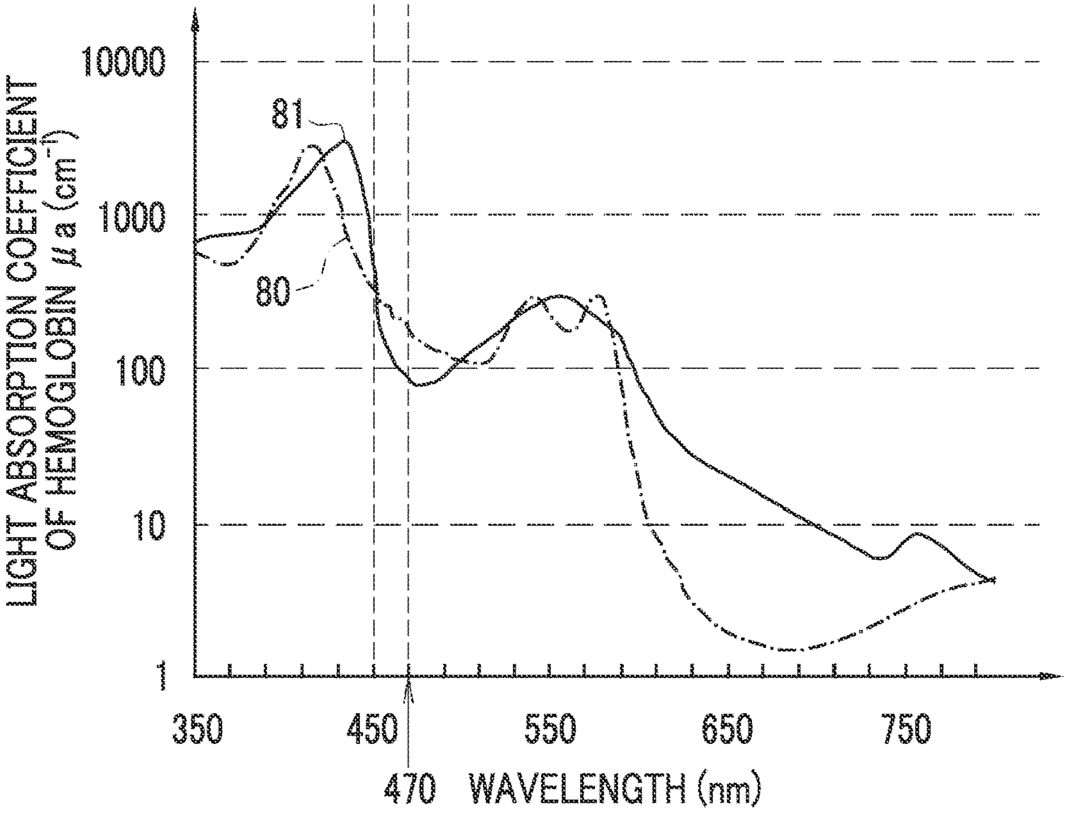
FIG. 9 is a graph showing light absorption coefficients of oxygenated hemoglobin and reduced hemoglobin.

The correlation is closely related to the light absorption characteristics and light scattering characteristics of oxygenated hemoglobin (graph 80) and reduced hemoglobin (graph 81) shown in FIG. 9. For example, since the amount of absorbed light is changed depending on the oxygen saturation of hemoglobin in a wavelength range in which a difference between the light absorption coefficient of oxygenated hemoglobin and the light absorption coefficient of reduced hemoglobin is large, such as a wavelength range of 470±10 nm of the second blue light BL, information about oxygen saturation is easily handled. Accordingly, oxygen saturation can be calculated using the signal ratio B2/G1 including the B2 image signals corresponding to the second blue light BL having a central wavelength of 470 nm. However, the signal ratio B2/G1 is highly dependent on not only oxygen saturation but also on a blood volume. Therefore, the signal ratio R1/G1 changing depending on mainly a blood volume is used in addition to the signal ratio B2/G1, so that oxygen saturation can be accurately obtained without being affected by a blood volume. The wavelength range of 540±20 nm of the green light included in the G1 image signal is a wavelength range in which the amount of absorbed light is likely to change depending on a blood volume since a light absorption coefficient of hemoglobin is relatively high.

Figure 10:
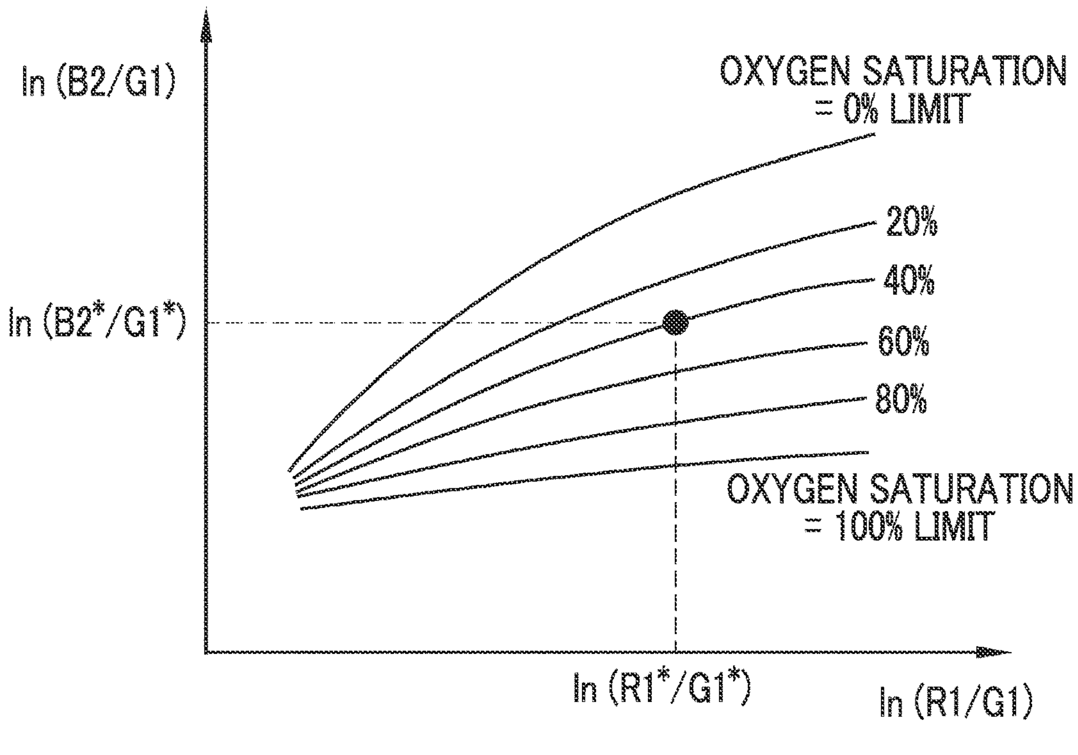
FIG. 10 is a diagram illustrating a method of calculating oxygen saturation.

The oxygen saturation-calculation section 71 calculates oxygen saturation corresponding to the signal ratios B2/G1 and R1/G1 for each pixel with reference to the oxygen saturation calculation table TBL. For example, as shown in FIG. 10, oxygen saturation corresponding to signal ratios B2*/G1* and R1*/G1* of a specific pixel is "40%". Accordingly, the oxygen saturation-calculation section 71 calculates the oxygen saturation of the specific pixel as "40%".

It is rare that the signal ratios B2/G1 and R1/G1 are extremely large or extremely small. That is, it is rare that a combination of the respective values of the signal ratios B2/G1 and R1/G1 is distributed below the isoline 77 (see FIG. 7) of an upper limit of an oxygen saturation of 100%, or conversely, is distributed above the isoline 78 (see FIG. 7) of a lower limit of an oxygen saturation of 0%. However, in a case where a combination of the values of the signal ratios B2/G1 and R1/G1 is distributed below the isoline 77 of the upper limit, the oxygen saturation-calculation section 71 calculates oxygen saturation as 100%. In a case where a combination of the values of the signal ratios B2/G1 and R1/G1 is distributed above the isoline 78 of the lower limit, the oxygen saturation-calculation section 71 calculates oxygen saturation as 0%. Further, in a case where a point corresponding to the signal ratios B2/G1 and R1/G1 is not distributed between the isoline 77 of the upper limit and the isoline 78 of the lower limit, oxygen saturation may be displayed to allow a user to understand that the reliability degree of oxygen saturation at the pixel is low, and may not be calculated.

The image generation section 72 generates an oxygen saturation image in which oxygen saturation is made as an image using the oxygen saturation that is calculated by the oxygen saturation-calculation section 71. Specifically, the image generation section 72 acquires B1 image signals, G1 image signals, and R1 image signals (corresponding to a normal image), and applies a gain corresponding to the oxygen saturation to these image signals for each pixel. Then, the image generation section 72 generates RGB image data using the B1 image signals, the G1 image signals, and the R1 image signals to which the gain is applied.

For example, the image generation section 72 multiplies all of the B1 image signals, the G1 image signals, and the R1 image signals by the same gain "1" at pixels where oxygen saturation is 60% or more. In contrast, the image generation section 72 multiplies the B1 image signals by a gain less than "1" and multiplies the G1 image signals and the R1 image signals by a gain of "1" or more at pixels where oxygen saturation is less than 60%. The RGB image data generated using the B1 image signals, the G1 image signals, and the R1 image signals subjected to this gain processing are the oxygen saturation image.

In the oxygen saturation image generated by the image generation section 72, a high-oxygen region (a region in which oxygen saturation is in the range of 60 to 100%) is represented by the same color as that in the normal image. On the other hand, a low-oxygen region (a region in which oxygen saturation is in the range of 0 to 60%) in which oxygen saturation is lower than a specific value is represented by a color (pseudo color) different from that in the normal image.

In the present embodiment, the image generation section 72 multiplies image signals by a gain that allows only a low-oxygen region to have a pseudo color. However, the image generation section 72 may apply a gain corresponding to oxygen saturation even in a high-oxygen region to allow the entire oxygen saturation image to have a pseudo color. Further, a low-oxygen region and a high-oxygen region are classified using an oxygen saturation of 60%, but this boundary is also arbitrary.

The specific colorant concentration-calculation section 73 calculates a specific colorant concentration of a specific colorant on the basis of the B3 image signals and the G1 image signals. The specific colorant concentration-calculation section 73 constantly calculates a specific colorant concentration during the oxygen saturation mode. The specific colorant is a colorant that is a colorant other than blood hemoglobin among colorants included in the subject of observation and that affects the calculation of oxygen saturation.

Figure 11:
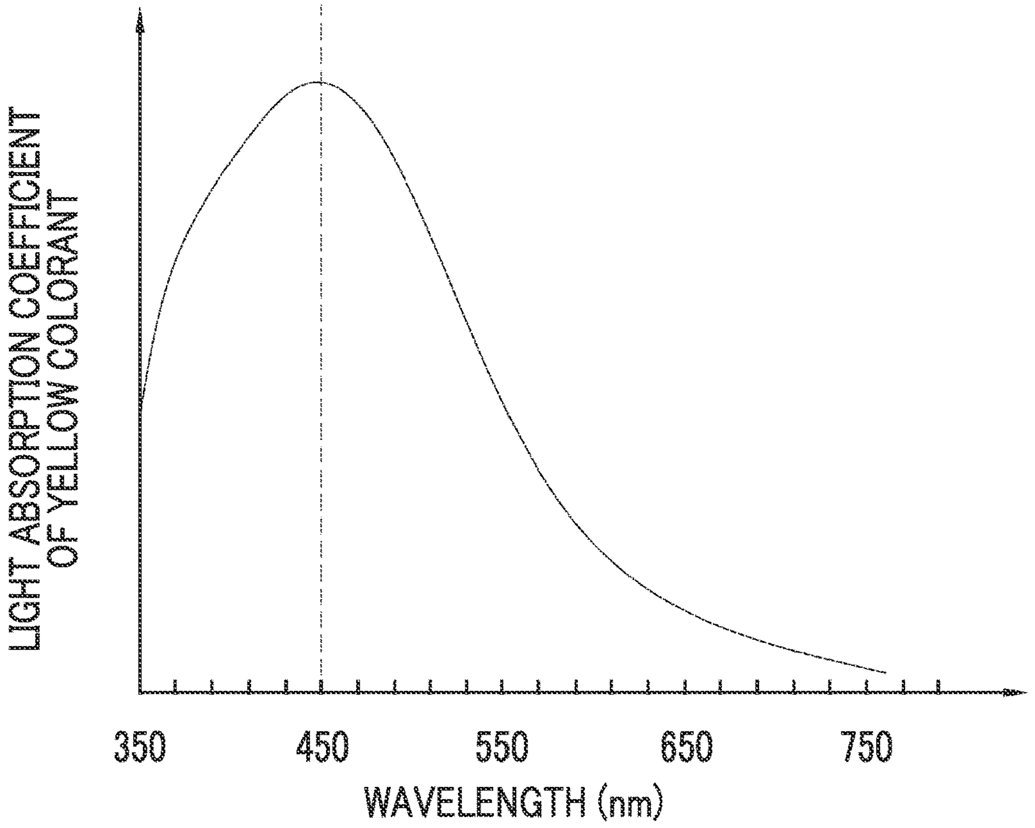
FIG. 11 is a graph showing a light absorption coefficient of a yellow colorant.

For example, a yellow colorant is included as the specific colorant. The light absorption coefficient of the yellow colorant has a peak at which a light absorption coefficient is at its maximum near a wavelength of 450±10 nm as shown in FIG. 11. Accordingly, a first wavelength range near a wavelength of 450±10 nm is a wavelength range in which the amount of absorbed light is likely to change depending on the concentration of the yellow colorant. Image information about the first wavelength range is included in the B3 image signal. Accordingly, in a case where the specific colorant is the yellow colorant, the specific colorant concentration-calculation section 73 calculates a signal ratio B3/G1 as the colorant concentration of the yellow colorant. A signal value of the signal ratio B3/G1 does not change depending on oxygen saturation, but changes depending on the concentration of the yellow colorant or on a blood volume.

Figure 12:
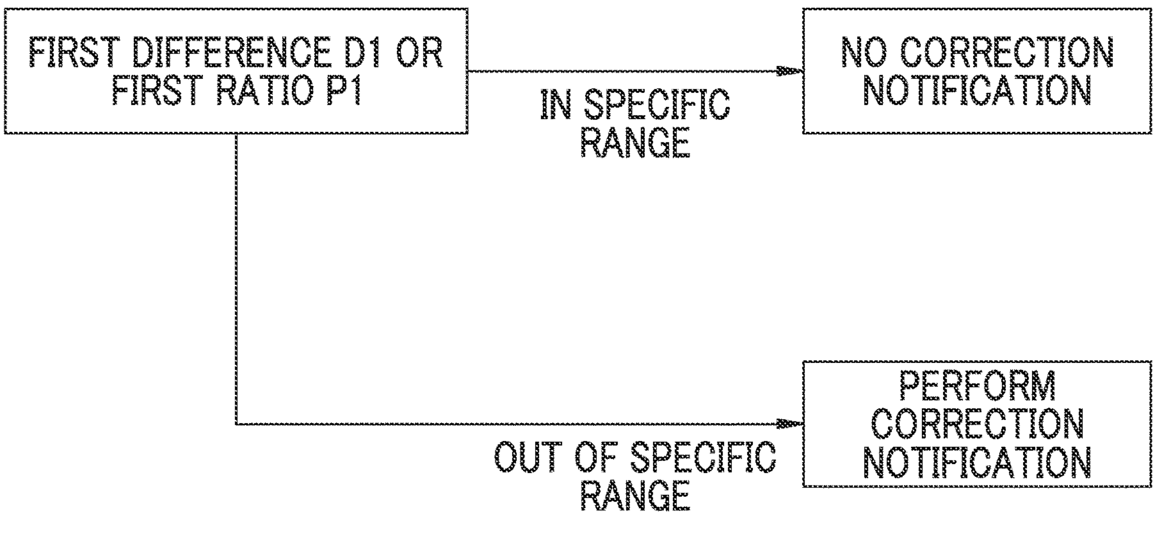
FIG. 12 is a diagram illustrating a correction notification.

The concentration monitoring section 74 monitors the specific colorant concentration during the calculation of oxygen saturation. The notification section 75 performs a correction notification related to the correction of the oxygen saturation calculation table TBL on the basis of the result of the monitoring of the specific colorant concentration. Specifically, it is preferable that the concentration monitoring section 74 calculates a first difference D1 (=|CX−CS|) or a first ratio P1 (CX/CS) between each of specific colorant concentrations CX sequentially calculated by the specific colorant concentration-calculation section 73 and a reference concentration CS predetermined for the specific colorant concentration. Then, as shown in FIG. 12, the notification section 75 does not perform a correction notification as long as the first difference D1 or the first ratio P1 is in a specific range. On the other hand, the notification section 75 performs a correction notification in a case where the first difference D1 or the first ratio P1 is out of the specific range.

Figure 13:
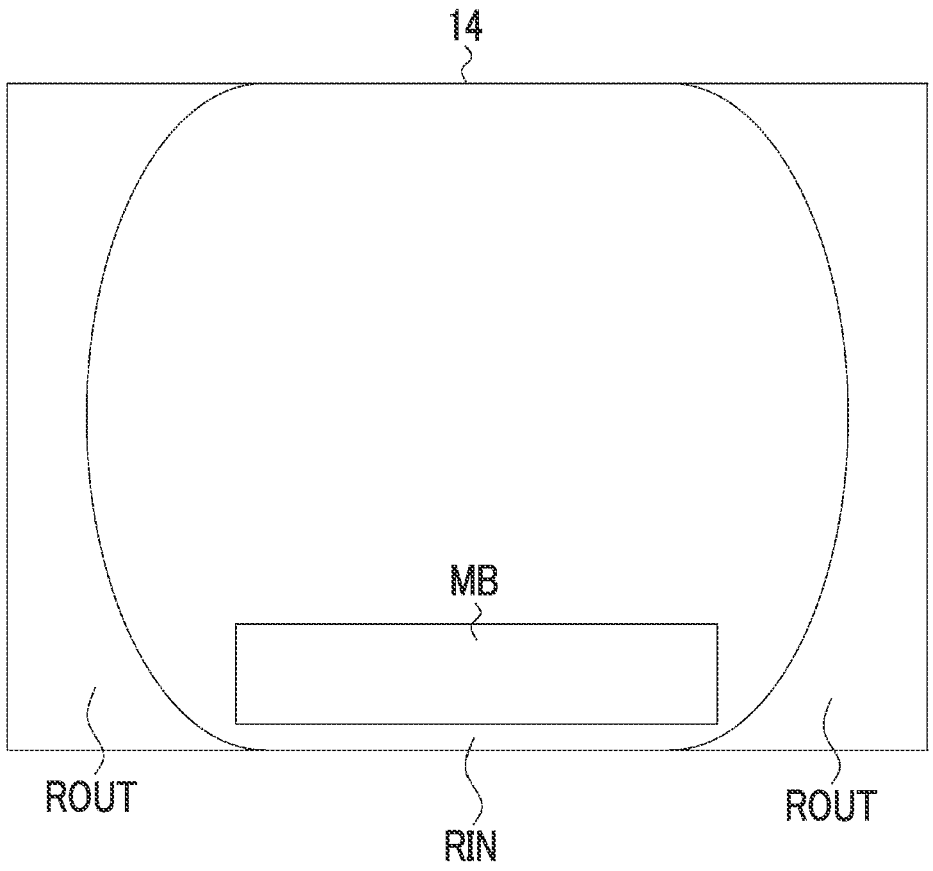
FIG. 13 is a diagram illustrating display of a message box that is one of the correction notifications.

It is preferable that the correction notification is performed by voice or by display on the display 15. For example, in a case where the correction notification is to be performed by display on the display 15, it is preferable that a small message box MB is displayed as a correction notification on the display 15 in a peripheral portion of an image display region RIN in which the oxygen saturation image or the like is displayed or in a portion ROUT other than the image display region so as not to hinder the observation of the oxygen saturation image as shown in FIG. 13 (in FIG. 13, the message box MB is displayed in the image display region RIN). It is preferable that the contents of the message box MB are contents for prompting a user to perform a tissue color correction (for example, "please operate the tissue color correction button **12*j***" or the like).

Further, the concentration monitoring section 74 may calculate a second difference D2 (=|Cave−CS|) or a second ratio P2 (Cave/CS) between an average value Cave of specific colorant concentrations calculated by the specific colorant concentration-calculation section 73 in a certain time and the reference concentration CS predetermined for the specific colorant concentration. The notification section 75 determines whether or not the second difference D2 or the second ratio P2 obtained for every certain time is in a specific range. Accordingly, since a correction notification is performed only in a case where the specific colorant concentration to be monitored is continuously maintained outside the specific range, there is no correction notification that is frequently performed in a case where the specific colorant concentration is out of the specific range due to a fluctuation in the specific colorant concentration caused by noise or a temporary change in an observation position.

Figure 14:
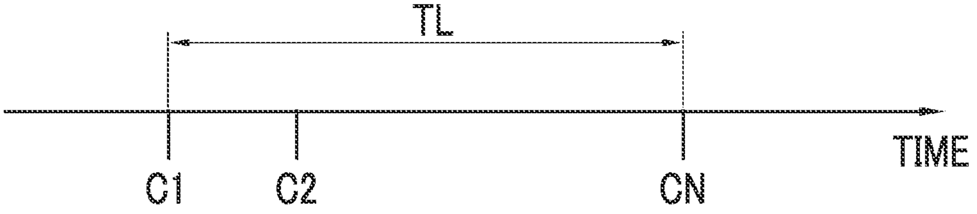
FIG. 14 is a diagram illustrating a specific colorant concentration that is calculated in a certain time TL.

The notification section 75 does not perform a correction notification as long as the second difference D2 or the second ratio P2 is in the specific range as in the case of the first difference or the first ratio P1. On the other hand, the notification section 75 performs a correction notification in a case where the second difference D2 or the second ratio P2 is out of the specific range. It is preferable that the average value Cave of the specific colorant concentrations is a value obtained in a case where the sum (C1+C2+ . . . +CN) of N specific colorant concentrations C1, C2, . . . , CN (N is a natural number) calculated in a certain time TL as shown in FIG. 14 by the specific colorant concentration-calculation section 73 is divided by N.

It is preferable that the reference concentration is a specific colorant concentration obtained at a timing when the oxygen saturation calculation table TBL is corrected. Specifically, it is preferable that a specific colorant concentration calculated by the specific colorant concentration-calculation section 73 at a timing when the tissue color correction button 12*j* is operated is used as the reference concentration. Further, it is preferable that the reference concentration is predetermined for each patient or each site. For example, since the state of a pretreatment (a state in which a yellow colorant remains) performed before an endoscopic diagnosis may differ depending on a patient, it is preferable that the reference concentration is changed for each patient in this case. Furthermore, in a case where an upper gastrointestinal tract, such as an esophagus or a stomach, is observed and a case where a lower gastrointestinal tract, such as a large intestine, is observed, a state in which a yellow colorant is included in the subject of observation may differ. For this reason, it is preferable that the reference concentration is changed for each site in this case. The reference concentration is changed in a case where a user operates the user interface 16.

Figure 15:
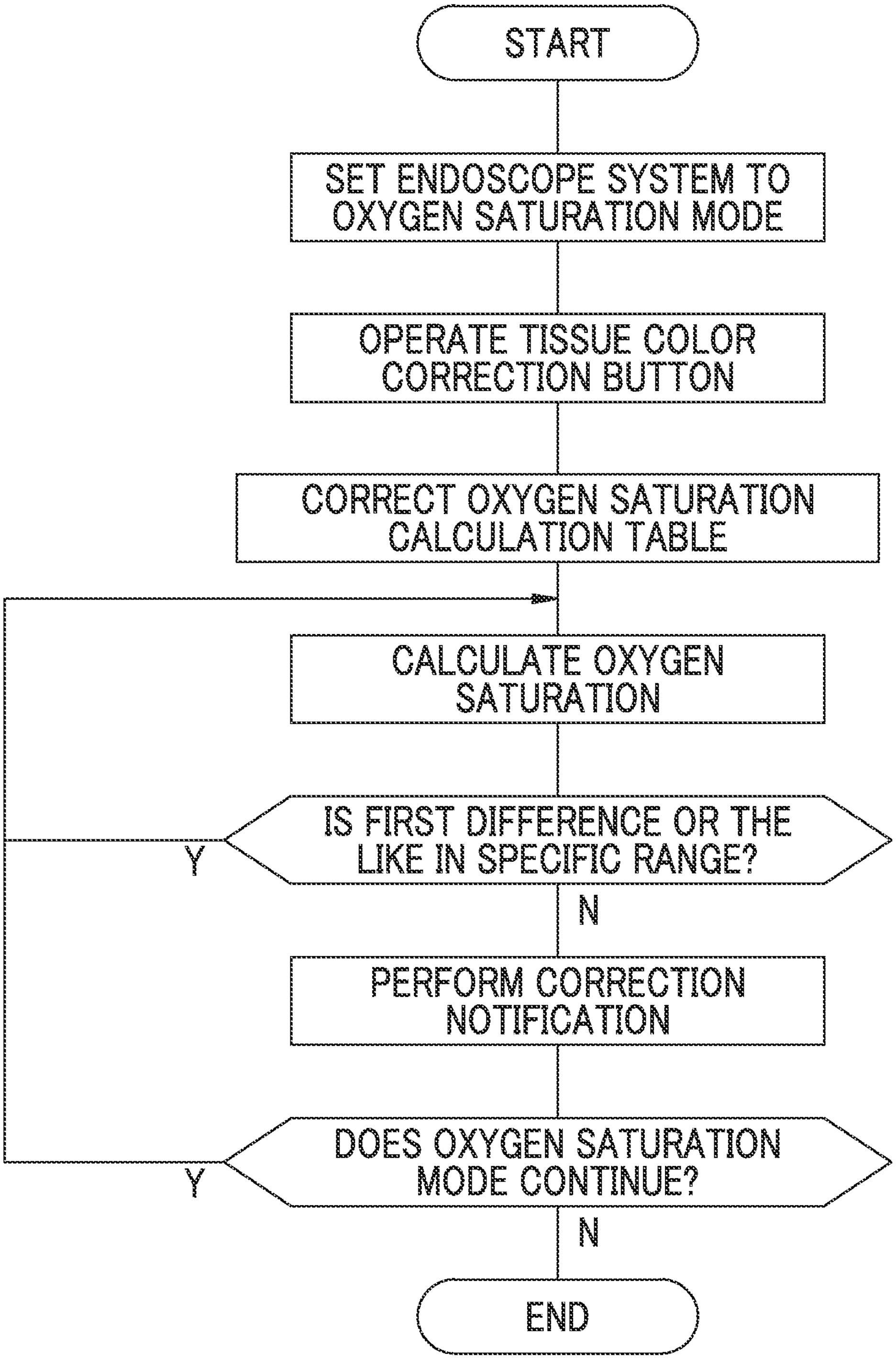
FIG. 15 is a flowchart showing a series of flows in the oxygen saturation mode.

Next, a series of flows of the oxygen saturation mode will be described with reference to a flowchart shown in FIG. 15. The endoscope system 10 is set to the oxygen saturation mode by the operation of the mode selector switch 12*f*. Accordingly, illumination having different light emission patterns and corresponding to three frames is applied to a subject of observation. A specific colorant concentration is calculated from image signals obtained with the illumination corresponding to these three frames. Then, before observing actual oxygen saturation, a user operates the tissue color correction button 12*j* in a state where a portion in which the user wants to observe oxygen saturation is in a visual field. A specific colorant concentration, which is calculated at a timing when the tissue color correction button 12*j* is operated, is used as a reference concentration, and the oxygen saturation calculation table TBL is corrected according to the reference concentration. Then, oxygen saturation is calculated with reference to the corrected oxygen saturation calculation table TBL on the basis of image signals obtained with the illumination corresponding to the three frames. The calculated oxygen saturation is made as an oxygen saturation image and is displayed on the display 15.

Then, whether or not the first difference D1 or the like between the specific colorant concentration and the reference concentration is in the specific range is monitored during the calculation of oxygen saturation. In a case where the first difference D1 or the like is in the specific range, the calculation of oxygen saturation continues without performing a correction notification. On the other hand, in a case where the first difference D1 or the like is not in the specific range, a correction notification is performed. In a case where a user considers that the oxygen saturation calculation table TBL is required to be corrected, the user operates the tissue color correction button 12*j* to re-correct the oxygen saturation calculation table TBL. A series of flows described above is repeatedly performed as long as the oxygen saturation mode continues.

Second Embodiment

In a second embodiment, a subject of observation is illuminated using a broadband light source, such as a xenon lamp, and a rotary filter instead of the four color LEDs 20*a* to 20*d* described in the first embodiment. Further, a subject of observation is imaged by a monochrome imaging sensor instead of the color imaging sensor 44. Other parts are the same as those of the first embodiment.

Figure 16:
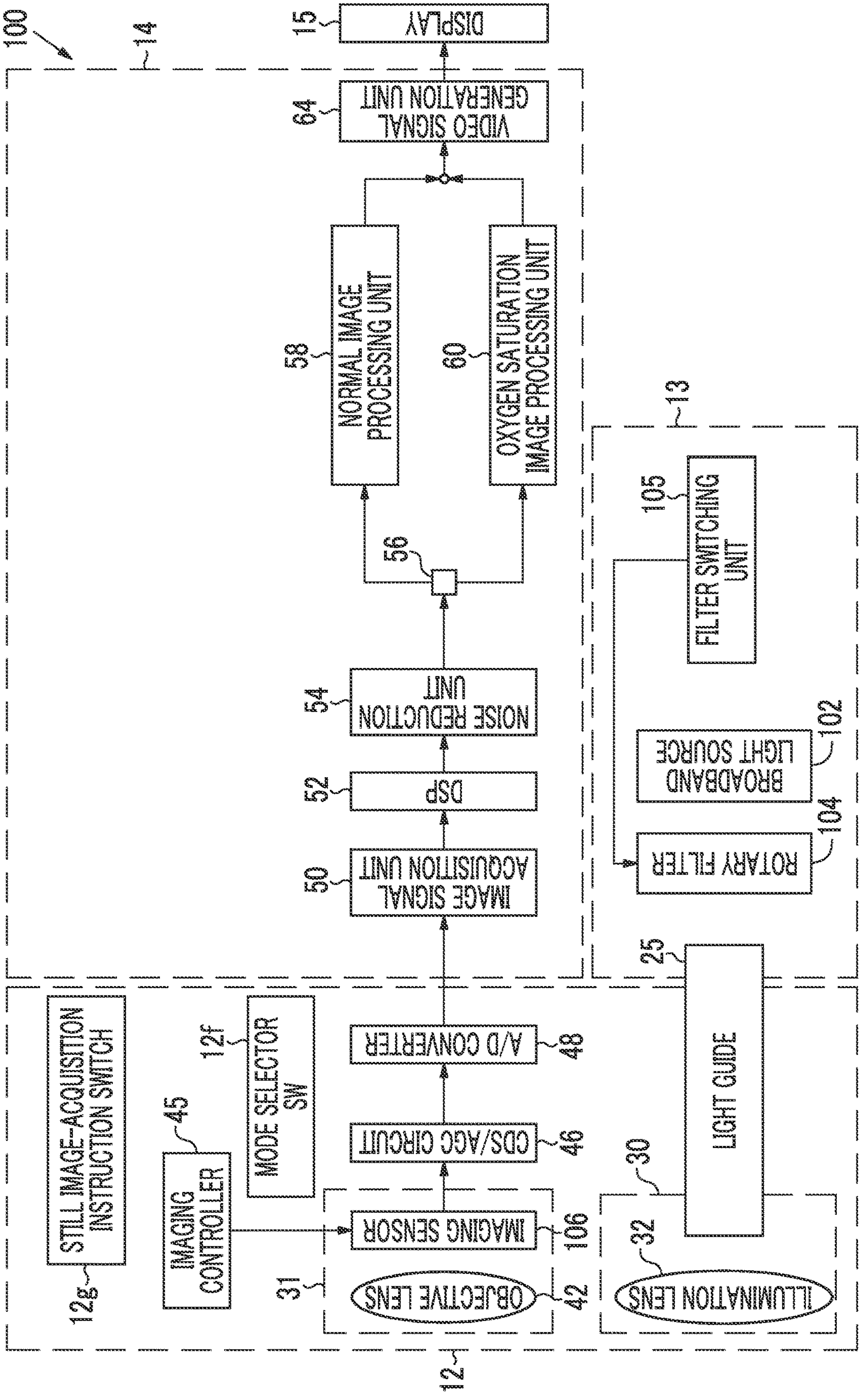
FIG. 16 is a block diagram showing functions of an endoscope system according to a second embodiment.

As shown in FIG. 16, in an endoscope system 100 according to the second embodiment, a light source device 13 is provided with a broadband light source 102, a rotary filter 104, and a filter switching unit 105 instead of the four color LEDs 20*a* to 20*d*. Further, an imaging optical system 31 is provided with a monochrome imaging sensor 106, which is not provided with a color filter, instead of the color imaging sensor 44.

The broadband light source 102 is a xenon lamp, a white LED, or the like, and emits white light of which the wavelength range reaches the wavelength range of red light from the wavelength range of blue light. The rotary filter 104 comprises an inner filter 108 provided inside and an outer filter 109 provided outside (see FIG. 17). The filter switching unit 105 moves the rotary filter 104 in a radial direction, inserts the inner filter 108 of the rotary filter 104 into an optical path of white light in a case where the endoscope system 100 is set to the normal mode by the mode selector SW 12*f*, and inserts the outer filter 109 of the rotary filter 104 into the optical path of white light in a case where the endoscope system 100 is set to the oxygen saturation mode.

Figure 17:
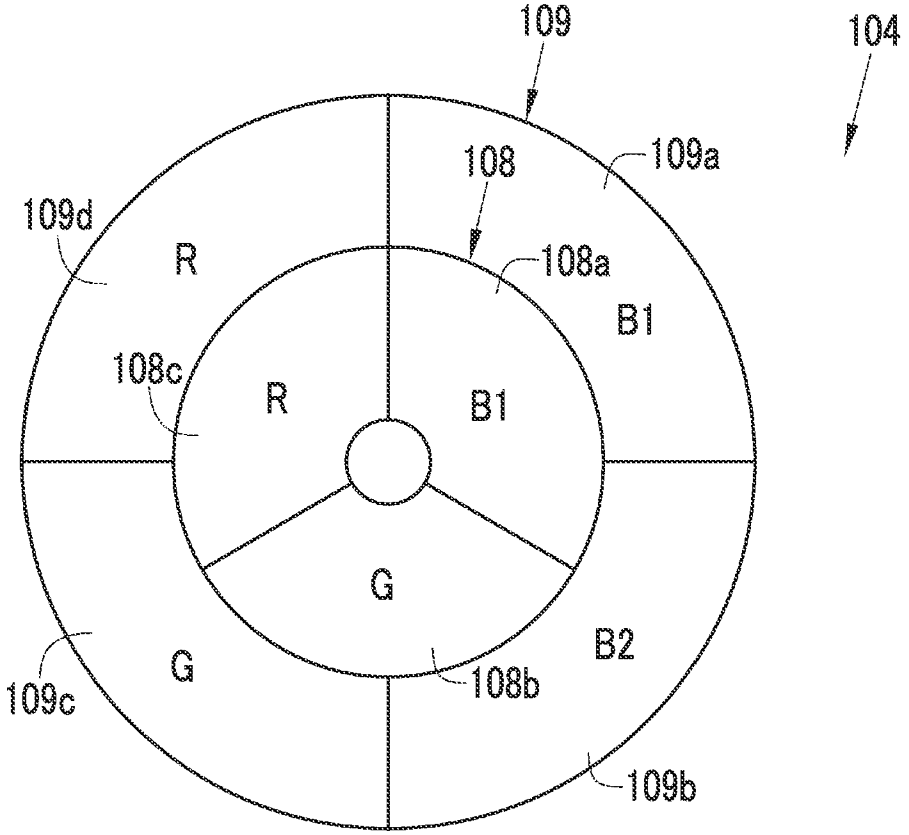
FIG. 17 is a plan view of a rotary filter.

As shown in FIG. 17, the inner filter 108 is provided with a B1 filter 108*a*, a G filter 108*b*, and an R filter 108*c* that are arranged in a circumferential direction. The B1 filter 108*a* transmits the first blue light BS of white light, the G filter 108*b* transmits the green light G of white light, and the R filter 108*c* transmits the red light R of white light. Accordingly, in the normal mode, the subject of observation is alternately irradiated with the first blue light BS, the green light G, and the red light R as the rotary filter 104 is rotated.

The outer filter 109 is provided with a B1 filter 109*a*, a B2 filter 109*b*, a G filter 109*c*, and an R filter 109*d* that are arranged in the circumferential direction. The B1 filter 109*a* transmits the first blue light BS of white light, the B2 filter 109*b* transmits the second blue light BL of white light, the G filter 109*c* transmits the green light G of white light, and the R filter 109*d* transmits the red light R of white light. Accordingly, in the oxygen saturation mode, the subject of observation is alternately irradiated with the first blue light BS, the second blue light BL, the green light G, and the red light R as the rotary filter 104 is rotated.

In the endoscope system 100, the subject of observation is imaged by the monochrome imaging sensor 106 whenever the subject of observation is illuminated with the first blue light BS, the green light G, and the red light R in the normal mode. Accordingly, Bc image signals, Gc image signals, and Rc image signals are obtained. Then, a normal image is generated on the basis of these three color image signals by the same method as in the first embodiment.

On the other hand, the subject of observation is imaged by the monochrome imaging sensor 106 whenever the subject of observation is illuminated with the first blue light BS, the second blue light BL, the green light G, and the red light R in the oxygen saturation mode. Accordingly, B3 image signals, B2 image signals, G1 image signals, and R1 image signals are obtained. An oxygen saturation image is generated on the basis of these four color image signals by the same method as in the first embodiment.

The hardware structures of the processing units, which perform various types of processing in the above-mentioned embodiments, such as the image signal acquisition unit 50, the noise reduction unit 54, the image processing switching unit 56, the normal image processing unit 58, the oxygen saturation image processing unit 60, the video signal generation unit 64, the calculation value-calculation section 70, the oxygen saturation-calculation section 71, the image generation section 72, the specific colorant concentration-calculation section 73, the concentration monitoring section 74, and the notification section 75, are various processors to be described below. Various processors include: a central processing unit (CPU) that is a general-purpose processor functioning as various processing units by executing software (programs); a graphics processing unit (GPU); a programmable logic device (PLD) that is a processor of which the circuit configuration can be changed after manufacture, such as a field programmable gate array (FPGA); a dedicated electrical circuit that is a processor having a circuit configuration designed exclusively to perform various types of processing; and the like.

One processing unit may be formed of one of these various processors, or may be formed of a combination of two or more processors of the same type or different types (for example, a plurality of FPGAs, a combination of a CPU and an FPGA, a combination of a CPU and a GPU, or the like). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, using one integrated circuit (IC) chip as typified by a system on chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined. Further, the hardware structure of the storage unit is a storage device, such as a hard disk drive (HDD) or a solid-state drive (SSD).

EXPLANATION OF REFERENCES

10: endoscope system
12: endoscope
12*a*: insertion part
12*b*: operation part
12*c*: bendable part
12*d*: distal end part
12*f*: mode selector switch
12*g*: still image-acquisition instruction switch
12*h*: zoom operation part
12*j*: tissue color correction button
13: light source device
14: processor device
15: display
16: user interface
20: light source unit
20*a*: BS-LED
20*b*: BL-LED
20*c*: G-LED
20*d*: R-LED
21: light source processor
23: optical path-combination unit
25: light guide
30: illumination optical system
31: imaging optical system
32: illumination lens
42: objective lens
44: imaging sensor
45: imaging controller
46: CDS/AGC circuit
48: A/D converter
50: image signal acquisition unit
52: DSP
54: noise reduction unit
56: image processing switching unit
58: normal image processing unit
60: oxygen saturation image processing unit
64: video signal generation unit
70: calculation value-calculation section
71: oxygen saturation-calculation section
72: image generation section
73: specific colorant concentration-calculation section
74: concentration monitoring section
75: notification section
77, 78: isoline
80, 81: graph
100: endoscope system
102: broadband light source
104: rotary filter
105: filter switching unit
106: imaging sensor
108: inner filter
108*a*: B1 filter
108*b*: G filter
108*c*: R filter
109: outer filter
109*a*: B1 filter
109*b*: B2 filter
109*c*: G filter
109*d*: R filter
BF: B color filter
GF: G color filter
MB: message box
RF: R color filter
RIN: image display region
ROUT: portion other than image display region
TBL: oxygen saturation calculation table

What is claimed is:

1. A processor device comprising:

one or more processors configured to:

receive image signals input from an endoscope;

remove noise from the image signals to output noise-removed image signals;

acquire, among the noise-removed image signals, a first image signal that corresponds to a first wavelength range having a sensitivity to a specific colorant concentration of a specific colorant other than blood hemoglobin among colorants included in a subject of observation, a second image signal that corresponds to a second wavelength range having a sensitivity to oxygen saturation of blood hemoglobin, a third image signal that corresponds to a third wavelength range having a sensitivity to a blood volume, and a fourth image signal that corresponds to a fourth wavelength range having a wavelength longer than wavelengths of the first wavelength range, the second wavelength range, and the third wavelength range;

calculate a calculation value via calculation processing based on the second image signal, the third image signal, and the fourth image signal;

calculate the oxygen saturation on the basis of the calculation value with reference to an oxygen saturation calculation table;

calculate a signal ratio of the first image signal to the third image signal as the specific colorant concentration on the basis of the first image signal and the third image signal; and monitor the specific colorant concentration during the calculation of the oxygen saturation by continuously calculating a first difference or a first ratio between the specific colorant concentration and a reference concentration, wherein the reference concentration is the specific colorant concentration obtained at a timing at which the oxygen saturation calculation table is corrected in response to an operation of a user; and a display, configured to perform a correction notification by displaying to the user on the display in response to determining that the first difference or the first ratio is out of a specific range.

2. The processor device according to claim 1, wherein the one or more processors configured to:

calculate a specific colorant concentration-average value that is an average value of specific colorant concentrations calculated in a certain time;

calculate a second difference or a second ratio between the specific colorant concentration-average value and a reference concentration predetermined for the specific colorant concentration; and perform the correction notification in a case where the second difference or the second ratio is out of a specific range.

3. The processor device according to claim 1, wherein the reference concentration is predetermined for each patient or each site.

4. The processor device according to claim 1, wherein the specific colorant is a yellow colorant.

5. The processor device according to claim 1, wherein the first wavelength range is 450±10 nm, the second wavelength range is 470±10 nm, the third wavelength range is a green light wavelength range, and the fourth wavelength range is a red light wavelength range.

6. An endoscope system comprising:

the processor device according to claim 1;

a light source device that includes a light source unit and a light source processor, the light source unit including a first semiconductor light source emitting first blue light, a second semiconductor light source emitting second blue light having a wavelength longer than a wavelength of the first blue light, a third semiconductor light source emitting green light, and a fourth semiconductor light source emitting red light, and the light source processor controlling turn-on and turn-off of the first semiconductor light source, the second semiconductor light source, the third semiconductor light source, and the fourth semiconductor light source; and an endoscope that includes an imaging sensor provided with a B color filter having a blue light transmission range, a G color filter having a green light transmission range, and an R color filter having a red light transmission range, wherein the first wavelength range is a wavelength range of light, which has been transmitted through the B color filter, of the green light, the second wavelength range is a wavelength range of light, which has been transmitted through the B color filter, of the second blue light, the third wavelength range is a wavelength range of light, which has been transmitted through the G color filter, of the green light, and the fourth wavelength range is a wavelength range of light, which has been transmitted through the R color filter, of the red light.

7. The endoscope system according to claim 6, wherein the blue light transmission range is 380 to 560 nm, the green light transmission range is 450 to 630 nm, and the red light transmission range is 580 to 760 nm.

8. A method of operating a processor device, the method, executed by one or more processors, comprising:

a step of receiving image signals input from an endoscope;

a step of removing noise from the image signals to output noise-removed image signals;

a step of acquiring, among the noise-removed image signals, a first image signal that corresponds to a first wavelength range having a sensitivity to a specific colorant concentration of a specific colorant other than blood hemoglobin among colorants included in a subject of observation, a second image signal that corresponds to a second wavelength range having a sensitivity to oxygen saturation of blood hemoglobin, a third image signal that corresponds to a third wavelength range having a sensitivity to a blood volume, and a fourth image signal that corresponds to a fourth wavelength range having a wavelength longer than wavelengths of the first wavelength range, the second wavelength range, and the third wavelength range;

a step of calculating a calculation value via calculation processing based on the second image signal, the third image signal, and the fourth image signal;

a step of calculating the oxygen saturation on the basis of the calculation value with reference to an oxygen saturation calculation table;

a step of calculating a signal ratio of the first image signal to the third image signal as the specific colorant concentration on the basis of the first image signal and the third image signal; and a step of monitoring the specific colorant concentration during the calculation of the oxygen saturation by continuously calculating a first difference or a first ratio between the specific colorant concentration and a reference concentration, wherein the reference concentration is the specific colorant concentration obtained at a timing at which the oxygen saturation calculation table is corrected in response to an operation of a user, and a step of performing a correction notification, via a display, by displaying to the user on the display in response to determining that the first difference or the first ratio is out of a specific range.

* * * * *